United States Patent [19]

Muller

[11] Patent Number: 4,945,187
[45] Date of Patent: Jul. 31, 1990

[54] PROCESS FOR PREPARING ENANTIOMERICALLY PURE PROPAN-1,2-DIOLS

[75] Inventor: Klaus R. Muller, Mannheim, Fed. Rep. of Germany

[73] Assignee: Karl Thomae GmbH, Biberach an der Riss, Fed. Rep. of Germany

[21] Appl. No.: 379,741

[22] Filed: Jul. 14, 1989

[30] Foreign Application Priority Data

Jul. 14, 1988 [DE] Fed. Rep. of Germany ....... 3823787

[51] Int. Cl.$^5$ ...................... C07C 29/36; C07C 31/20; C07C 29/76; C07C 29/80
[52] U.S. Cl. ..................................... 568/868; 568/864
[58] Field of Search ................................ 568/864, 868

[56] References Cited

U.S. PATENT DOCUMENTS

| 2,683,721 | 7/1954 | Schlesinger et al. | 568/864 |
| 4,156,791 | 5/1979 | Childs | 568/864 |
| 4,313,891 | 2/1982 | Dozzi et al. | 568/864 |

FOREIGN PATENT DOCUMENTS

| 1341174 | 9/1987 | U.S.S.R. | 568/864 |

Primary Examiner—J. E. Evans
Attorney, Agent, or Firm—David E. Frankhouser; Daniel Reitenbach; Mary-Ellen M. Timbers

[57] ABSTRACT

The invention relates to a process for preparing enantiomerically pure S(+)-propan-1,2-diol and R(−)-propan-1,2-diol from L(−)-lactide or D(+)-lactide, respectively.

8 Claims, No Drawings

PROCESS FOR PREPARING ENANTIOMERICALLY PURE PROPAN-1,2-DIOLS

The invention relates to a process for preparing enantiomerically pure S(+)-propan-1,2-diol and R(−)-propan-1,2-diol from L(−)-lactide and D(+)-lactide, respectively.

Enantiomerically pure propane diols are useful reagents in stereospecific methods of synthesis. Thus, for example, S(+)-propan-1,2-diol is used in the preparation of the calcium blocker verapamil and gallopamil [L. J. Theodore and W. L. Nelson, J. Org. Chem. 52 (1987) 1309].

Up till now, propane diols of low optical purity have been prepared by reducing the corresponding lactic acid esters with complex hydrides [J. Gambos, E. Haslinger and U. Schmidt, Chem. Ber. 109 (1976) 2645] or hydrogen boride [C. Melchiorre, Chem. Ind. (London) 1976. 218]. Methods of preparation which start from propylene glycol ketals yield the corresponding propan-1,2-diols with only a low degree of purity [P. Newman, Optical Resolution Procedures for Chemical Compounds, Vol. 3: Alcohols, Phenols, Thiols, Aldehydes and Ketones, Optical Resolution Information Center, Manhattan College, Riverdale, N.Y. 1984, p. 23].

The aim of this invention is to provide a process which yields S(+)-propan-1,2-diol and R(−)-propan-1,2-diol with a high degree of optical purity.

According to the invention this objective is achieved by reacting L(−)-lactide or D(+)-lactide with a reducing agent, working up the reaction mixture by methods known per se and isolating the reaction products.

The reaction is preferably carried out in inert solvents. The resulting reaction mixture is subsequently worked up by hydrolysis and the propan-1,2-diols forms are isolated by distillation, after the solid reaction products have been separated off.

By contrast with the methods known from the prior art for preparing enantiomerically pure propan-1,2-diols, by using the process according to the invention S(+)-propan-1,2-diol or R(−)-propan-1,2-diol is obtained in a higher degree of optical purity, thus allowing the propan-1,2-diols prepared according to the invention to be used directly in stereospecific syntheses.

The starting materials used are L(−)-lactide or D(+)-lactide in an optical purity of more than 99.5%.

The reducing agents used are hydrogen boride, such as the borane dimethylsulphide complex, and complex hydrides such as lithium borohydride (LiBH$_4$), Vitride ® (NaAlH$_2$(OCH$_2$CH$_2$OCH$_3$)$_2$), sodium borohydride (NaBH$_4$), lithium aluminium hydride (LiAlH$_4$) and preferably diisobutyl aluminium hydride (DIBAH) and silanes, such as triethoxysilane HSi(OCH$_2$CH$_3$)$_3$.

In the reduction of the L(−)-lactide or D(+)-lactide the reducing agent is advantageously used in excess. Preferably, when diisobutyl aluminium hydride is used, 4.1 to 4.3 mol—or an equivalent quantity of another reducing agent—is used for each mol of L(−)-lactide or D(+)-lactide.

The inert solvents used are expediently aromatic or aliphatic hydrocarbons such as toluene, xylene or heptane or water-immiscible ethers such as di-n-butylether and anisole.

When complex hydrides are used, depending on the reactivity of the hydride used, the reduction is carried out in a temperature range from ambient temperature to the boiling point of the reaction mixture and preferably within the range from 40° to 70° C.

The L(−)-lactide or D(+)-lactide is conveniently suspended in an inert solvent under an inert gas atmosphere and the reducing agent, which may be dissolved or suspended in an inert solvent, is slowly added thereto with stirring, and stirring is continued for a sufficient length of time to allow the reduction to be completed. The reactants may also be added in the reverse order. The temperature may be kept within the range necessary for reduction by means of a thermostat.

The reaction mixture is then hydrolysed with a basically reacting aqueous solution of a suitable alkali metal or alkaline earth metal compound, such as sodium hydroxide solution, and stirred at elevated temperature in order to complete the hydrolysis.

The organic phase is then separated off and, if alkali metal aluminium hydrides are used, the pH of the aqueous phase is adjusted to a value of about pH 6 using an inorganic acid or an organic acid or an aqueous solution thereof in order to precipitate and separate off the aluminium hydroxide. The aluminium hydroxide is separated off using suitable separating means, for example a suction filter charged with kieselguhr or cellulose (Diacel ®) and washed with water.

The reaction solution or the combined filtrates are evaporated down in vacuo. The residue remaining is suspended in a suitable solvent, e.g. an alcohol, preferably ethanol or isopropanol, then suction filtered and washed.

The solvent is then removed under reduced pressure and the residue remaining is distilled in vacuo.

Purification by distillation yields S(+)-propan1,2-diol or R(−)-propan-1,2-diol in the form of colourless oils.

The Examples which follow serve to illustrate the invention without restricting it.

EXAMPLE 1

S(+)-propan-1,2-diol 43.2 g (0.3 mol) of L(−)-lactide [optical purity more than 99.5%] are suspended in 200 ml of toluene and slowly 1038 ml of a 20% solution (1.24 mol) of diisobutyl aluminium hydride in toluene is added thereto with stirring. The temperature of the reaction mixture is maintained in the range between 40° and 50° C. by means of a cooling mixture of dry ice and isopropanol. After the addition has ended, the reaction mixture is stirred for a further hour at 40° to 50° C. to complete the reduction. The mixture is then hydrolysed with 840 ml of 3N sodium hydroxide solution, the reaction mixture being added over a period of 40 minutes to the aqueous solution of sodium hydroxide and the temperature being maintained in the range from 75° to 80° C. during this addition. In order to complete the hydrolysis the mixture is stirred for a further 30 minutes at a temperature from 65° to 80° C. and is then adjusted to pH 6 using 300 g of a 32% by weight solution of hydrogen chloride in water.

The aluminium hydroxide thus precipitated is suction filtered using a filter charged with kieselguhr (Diacel ®) and washed with 750 ml of water. The filtrate is evaporated down under reduced pressure and the residue resulting is suspended in 100 ml of cold ethanol, suction filtered and washed with 50 ml of ethanol.

After the solvent has been distilled off in vacuo. a yellowish-brown oil is obtained which, after distillation under a reduced pressure of 1 to 2 hPa in a boiling range of 50° to 60° C., yields 31.3 g of a colourless oil having a specific rotation of $[\alpha]_D 20 = 17.3$ and a yield of 69% of theory.

EXAMPLE 2

R(−)-prop-an-1,2-diol is prepared analogously to Example 1 but using D(+)-lactide instead of L(−)-lactide as the starting material.

31.3 g (69% of theory) of the R(−)-propane diol are isolated in the form of a colourless oil with a rotation of $[\alpha]_D 20 = -17.2°$.

What is claimed is:

1. A process for preparing enantiomerically pure S(+)-propan-1,2-diol which comprises reacting L(−)-lactide with a reducing agent and then isolating the enantiomerically pure S(+)-propan-1,2-diol.

2. A process as recited in claim 1 which comprises the steps of:
   (a) reacting L(−)-lactide with a reducing agent, in an inert first solvent at a temperature of between about 40° C. and about 70° C. to produce a first reaction mixture;
   (b) hydrolysing the first reaction mixture with an aqueous solution of an alkali metal or alkaline earth metal, to form a second reaction mixture comprising an aqueous phase and an organic phase;
   (c) separating the aqueous phase from the organic phase;
   (d) separating out any aluminum hydroxide from the aqueous phase by precipitation;
   (e) concentrating the aqueous phase by evaporation to produce a residue;
   (f) suspending the residue in a second solvent to produce a suspension;
   (g) filtering the suspension to remove solid reaction products;
   (h) removing the second solvent from the filtered suspension to produce a filtrate; and
   (i) purifying the filtrate by distillation, to produce an enantiomerically pure S(+)-propan-1,2-diol.

3. A process for preparing enantiomerically pure R(−)-propan-1,2-diol which comprises reacting D(+)-lactide with a reducing agent and then isolating the enantiomerically pure R(−)-propan-1,2-diol.

4. A process as recited in claim 3 which comprises the steps of:
   (a) reacting D(+)-lactide with a reducing agent, in an inert solvent at a temperature of between about 40° C. and about 70° C. to produce a first reaction mixture;
   (b) hydrolysing the first reaction mixture with an aqueous solution of an alkali metal or alkaline earth metal, to form a second reaction mixture comprising an aqueous phase and an organic phase;
   (c) separating the aqueous phase from the organic phase;
   (d) separating out any aluminum hydroxide from the aqueous phase by precipitation;
   (e) concentrating the aqueous phase by evaporation to produce a residue;
   (f) suspending the residue in a second solvent to produce a suspension;
   (g) filtering the suspension to remove solid reaction products;
   (h) removing the second solvent from the filtered suspension to produce a filtrate; and
   (i) purifying the filtrate by distillation, to produce an enantiomerically pure R(−)-propan-1,2-diol.

5. A process as recited in claim 1 wherein the reducing agent is a silane, a borane, a complex borane, an aluminum hydride, a complex boron, or a complex aluminum hydride.

6. A process as recited in claim 2 wherein the reducing agent is a silane, a borane, a complex borane, an aluminum hydride, a complex boron, or a complex aluminum hydride.

7. A process as recited in claim 3 wherein the reducing agent is a silane, a borane, a complex borane, an aluminum hydride, a complex boron, or a complex aluminum hydride.

8. A process as recited in claim 4 wherein the reducing agent is a silane, a borane, a complex borane, an aluminum hydride, a complex boron, or a complex aluminum hydride.

* * * * *